(12) United States Patent  (10) Patent No.: US 7,437,913 B2
Djennati et al.  (45) Date of Patent: Oct. 21, 2008

(54) METHOD AND DEVICE FOR ANALYSING A LIQUID

(75) Inventors: Nasr-Eddine Djennati, Altrincham (GB); Jonathan Andrew Fuller, Amulree (GB); Robert Andrew Porter, Rushden (GB); David Scott, Witney (GB)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

(21) Appl. No.: 10/722,106

(22) Filed: Nov. 25, 2003

(65) Prior Publication Data

US 2005/0015000 A1  Jan. 20, 2005

(30) Foreign Application Priority Data

Jun. 6, 2003  (GB) ................. 0313015.0

(51) Int. Cl.
*G01N 33/86* (2006.01)
(52) U.S. Cl. ..................................... 73/64.41
(58) Field of Classification Search ............... 73/61.66; 324/204, 207.21
See application file for complete search history.

(56) References Cited

U.S. PATENT DOCUMENTS

| 4,319,194 A | 3/1982 | Cardinal et al. ............ 324/449 |
| 4,849,340 A | 7/1989 | Oberhardt .................... 435/13 |
| 5,039,617 A | 8/1991 | McDonald et al. ........... 436/69 |
| 5,110,727 A | 5/1992 | Oberhardt |
| 5,350,676 A * | 9/1994 | Oberhardt et al. ............. 435/13 |
| 5,504,011 A | 4/1996 | Gavin et al. |
| 5,534,226 A | 7/1996 | Gavin et al. ................... 422/73 |
| 5,800,781 A | 9/1998 | Gavin et al. |
| 5,841,023 A | 11/1998 | Parker et al. |
| 6,060,323 A | 5/2000 | Jina ............................ 436/69 |
| 6,136,271 A | 10/2000 | Lorincz et al. |
| 6,165,795 A * | 12/2000 | Mize et al. .................... 436/69 |
| 2002/0119486 A1* | 8/2002 | Oberhardt ....................... 435/6 |
| 2003/0044871 A1* | 3/2003 | Cutsforth et al. ............. 435/13 |
| 2005/0155415 A1 | 7/2005 | Kurowski et al. |

FOREIGN PATENT DOCUMENTS

EP  0 400 847  5/1990

OTHER PUBLICATIONS

Puckett et al., Monitoring Blood Coagulation With Magnetoelastic Sensors, Biosensors and Bioelectronics 18 (2003) pp. 675-681.

* cited by examiner

*Primary Examiner*—Hezron E. Williams
*Assistant Examiner*—Paul M West
(74) *Attorney, Agent, or Firm*—Foley Hoag LLP

(57) ABSTRACT

Novel methods and devices comprising magnetic particles for detecting or monitoring the coagulation state of a sample are provided.

29 Claims, 12 Drawing Sheets

METHOD AND DEVICE FOR ANALYSING A LIQUID

RELATED APPLICATIONS

This application claims the benefit of priority to U.K. Patent Application serial number 0313015.0, filed on Jun. 6, 2003, the content of which is hereby incorporated by reference in its entirety.

BACKGROUND OF THE INVENTION

Thrombosis is one of the leading causes of death worldwide. Cardiovascular events such as acute coronary syndromes as well as ischaemic cerebral infarctions are characterised by rupture or erosion of vulnerable atherosclerotic plaques and subsequent thrombosis. Thrombus formation impedes the flow of blood to vital organs and tissues, restricting oxygen supply and resulting ultimately in cell necrosis. It can be especially life threatening when this occurs in the lower body, heart, lungs or brain resulting respectively in deep vein thrombosis, acute myocardial infarction, pulmonary embolism or acute ischaemic stroke.

Various risk factors associated with atherosclerosis include hypercholesterolaemia, nitric oxide formation, smoking, as well as genetic factors. Thus certain individuals are at a higher risk of developing cardiac or vascular diseases than others.

Two pathways or coagulation cascades lead to the formation of a clot, known as the intrinsic and extrinsic pathways. These two pathways are initiated by distinct mechanisms but converge along a common pathway. Clot formation in response to an abnormal vessel wall in the absence of tissue injury is the result of the intrinsic pathway and clot formation in response to tissue injury is the result of the extrinsic pathway. The coagulation cascades are very complex and involve a number of different proteins known as clotting factors.

People who suffer from cardiac or vascular diseases and patients that have undergone surgical procedures are at risk of developing blood clots that may result in life-threatening clinical conditions. Such people are often treated with blood-thinning or anticoagulant drugs such as warfarin or aspirin. However, the amount of anticoagulant in the bloodstream must be maintained at the proper level: Too little may result in unwanted clotting whilst too much can result in haemorrhaging with life threatening consequences. As a result routine coagulation screening tests have been developed in order to evaluate the coagulation state of blood or plasma.

Clotting is a way by which the body closes off injured blood vessel walls following vascular injury. A blood clot consists of a plug of platelets enmeshed in a network of insoluble fibrin particles. The substance used in the blood to form a clot is fibrinogen, a protein synthesised by the liver which is cleaved by the enzyme thrombin to form fibrin peptides during normal coagulation. Thrombin also activates fibrin stabilising factor (Factor XIII) which subsequently cross-links the fibrin into a complex lattice. During clotting, fibrin strands start to form within the blood causing it to thicken. In time the thickened blood develop into a clot. Whilst formation of the clot is essential, the persistence of such clots is dangerous to the body. Thus, in order to minimise damage to the body after the clotting process has served its purpose, healthy cells surrounding the clot release plasmin to digest fibrin, therefore dissolving the clot.

A useful measure of coagulation is the so-called prothrombin time (PT) test and is routinely performed on patients who are on warfarin therapy following a cardiovascular event. The PT test measures the tissue factor-induced coagulation time of blood or plasma. This can provide an assessment of the extrinsic coagulation pathway and is sensitive to factors I, II, V, VII and X. The test is performed by adding a clotting agent such as thromboplastin and Ca2+ to a patient sample and then measuring the time for clot formation. Portable coagulation monitors such as the CoaguChek Plus™ coagulation meter have been developed which measure prothrombin time using non-anticoagulated capillary whole blood from a fingerstick or lancing device. Such monitors have been shown to be a valuable tool for patients on long-term oral anti-coagulation therapy.

However, the traditional expression of PT test results is inadequate for international comparison because the values depend upon the nature of the thromboplastin used. This has lead to the adoption of the Internationalised Normalised Ratio or INR as a way of expressing prothrombin time. INR is defined by $$INR = (\text{observed PT ratio})^{\exp ISI}$$

where ISI is the International Sensitivity Index and PT ratio=Patient's PT/Mean Normal PT.

The ISI is derived from the calibration line of the value of PT for a number of samples, obtained using a particular thromboplastin versus the World Health Organisation (WHO) international reference preparation for thromboplastin (human combined 67/40). A particular value of ISI, which takes into account the particular method and type of thromboplastin used, is assigned to each PT system, whereby each PT ratio can be translated into a standardised ratio. By employing INR, patients should be able to maintain a satisfactory level of coagulation which is independent of the PT system used. A PT and therefore INR value higher than normal means that the blood is taking longer than usual to form a clot. The normal value for the INR is 1.0 with values recommended between 2.5 and 3.5 for patients with prosthetic heart valves. The value of INR may be used to adjust the warfarin dose to bring a patient to within a recommended range, although other factors such as the levels of Vitamin K may need to be considered.

Another method of measurement of coagulation in either blood or plasma is the Activated Partial Thromboplastin Time Test (APTT). This test is a measure of the time of coagulation that occurs when the intrinsic pathway is activated. This is achieved by the addition of an activator (kaolin) to the sample in the presence of calcium ions and phospholipid (partial thromboplastin). APTT is used to evaluate the intrinsic coagulation pathway which includes the factors I, II, V, VIII, IX, X, XI and XII. Formation of complexes on the surface of the phospholipid enables prothrombin to be converted into thrombin, which results in clot formation.

APTT is used as a routine test for monitoring heparin therapy during surgical procedures, as a preoperative screening test for bleeding tendencies and to assess the overall competence of the patient's coagulation system. This test is commonly carried out in the central laboratory.

The Activated Clotting Time Test (ACT) resembles the APTT test and is used to monitor a patient's coagulation state during procedures that involve the dosing of high amounts of heparin, such as percutaneous transluminal coronary angioplasty (PCTA) and cardiopulmonary bypass surgery. The ACT test is considered as one of the best laboratory tests for the control of heparin therapy, both for patients undergoing treatment for thromboembolic disease and for those on extra-corporeal circulation. For those patients taking heparin, prolongation of the ACT is directly proportional to the concentration of heparin in blood. Monitoring is important and underdosing or overdosing of heparin may result respectively in pathological thrombus formation or serious hemorrhagic conditions.

The Thrombin Time Test (TT) measures the rate of formation of a fibrin clot in plasma by the action of thrombin on fibrinogen, compared to a normal plasma control. The test is performed by adding a standard amount of thrombin to a patient's plasma that has been deprived of platelets and measuring the time for a clot to form. It has been used in the diagnosis of disseminated intravascular coagulation and liver disease and is generally performed in the central laboratory.

Other clotting tests have been developed which target specific factors such as factor VIIIa which is indicative of factor IX deficiency. Another example is an assay for factor VIII, which constitutes a test for haemophilia. Other tests include assays to measure the levels of activation peptide factor IXa, antithrombin, protein C and protein S. Immunochemical assays have also been developed to identify and measure the various markers of coagulation and thrombosis.

Screening for platelet function is an important and common hematological test. Platelets are colourless cell fragments of about 2-4 um in diameter and are present in blood. Normal platelet counts range from 180,000-400,000/uL, however a platelet count of 50,000/uL is sufficient for normal hemostasis. After vascular damage, for example after surgery, higher platelet counts are needed, sometimes in excess of 100,000/uL. The purpose of platelets is to repair gaps in the blood vessel wall by either adhering to themselves or to damaged tissue. When cells become damaged, they release certain chemicals which cause the platelets to change from a discoid to a spherical form and become sticky, known as the aggregation-adhesion reaction.

Platelets are thought to play an important role in the pathogenesis of isechemic heart disease. Acute myocardial infarctions and unstable angina are clinical conditions associated with increased concentrations of certain platelet factors. Furthermore platelet dysfunction is one of the several major causes of bleeding after cardiopulmonary bypass. Platelets are also thought to contribute to the long-term process of atherogenesis by the release of growth factors and platelet function may also be influenced by high and low density lipoproteins. Thus screening for platelet function is an important and common hematological test.

Various instruments have developed for use in the laboratory and as point of care testing (POCT). In addition to this, devices have been developed which allow the patients to home-monitor their blood coagulation. Examples of such are exemplified below.

U.S. Pat. No. 5,534,226 assigned to International Technidyne Corporation, discloses an device and method for performing a coagulation time test on a blood sample whereby the blood is deposited into a capillary via a reservoir disposed within a disposable cuvette. The sample is then caused to reciprocally move within the capillary and blood forced to transverse a restricted region. Coagulation is determined to have occurred when the time required to transverse the restricted region is a predetermined percentage longer than the previous time.

U.S. Pat. No. 6,060,323 assigned to Hemosense, discloses a single use electronic device and test card for the measurement of the coagulation or lysis of a blood sample, typically 15 uL in volume. The sample is caused to contact electrodes, which measure the change in impedance corresponding to the change of viscosity of the sample as it clots.

U.S. Pat. No. 4,849,340, assigned to Cardiovascular Diagnostics, discloses a reaction slide for use with an device for the optical determination of prothrombin time. The reaction slide comprises a reaction chamber containing a dry reagent matrix in which are embedded a plurality of homogeneously distributed magnetic particles. Under the influence of a magnetic field from a permanent magnet, providing a field parallel to the base of the slide the particles are said to lie down against the base of the slide and under the influence of an electromagnet providing a field orthogonal to that of the permanent magnet, the particles are said to stand upright. A resulting change in light intensity due to the light scattering effects of the magnetic particles in their two orientations is detected.

U.S. Pat. No. 5,039,617 assigned to Biotrack discloses a device and method for carrying out the determination of activated partial thromboplastin time (APTT) on a whole blood sample by applying the sample to a capillary track contained in a housing, wherein clotting time is measured by the cessation of blood flow in the capillary track.

U.S. Pat. No. 4,319,194 discloses an aggregometer which is able to carry out platelet analysis on whole blood. Wire shaped electrodes are inserted into the blood sample to which an aggregating agent is added and the change in impedance is recorded as a function of time.

SUMMARY OF THE INVENTION

The present invention relates to a method of determining when a sample of liquid has coagulated, to the use of at least one magnetic field sensor to detect the movement and/or position of at least one particle within a liquid in order to determine the coagulation state of a liquid, to a device for determining the coagulation state of a liquid, to an assay test strip suitable for use with an assay reader, to apparatus for determining the coagulation time of blood or plasma, and to a method of determining the coagulation time of blood or plasma.

More particularly but not exclusively there is disclosed a method and device for analysing a liquid sample to determine the presence of a disease state which results in a change in coagulation state of the liquid. In certain embodiments, the method and device may be used to determine a disturbance of hemostasis, such as for example, by measuring the coagulation or prothrombin time (PT) of a sample of blood or plasma. Other disturbances of hemostasis that may be determined include measurement of the degree of platelet aggregation, the rate or amount of clot formation and/or clot dissolution, the time required for forming a fibrin clot, the activated partial thromboplastin time (APTT), the activated clotting time (ACT), the protein C activation time (PCAT), the Russell's viper venom time (RVVT) and the thrombin time (TT).

Also within the scope of the present invention are kits for the practice of the methods of the invention, as well as kits comprising the devices of the invention.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

In order that the invention may be more clearly understood embodiments thereof will now be described by way of example with reference to the accompanying drawings of which.

DETAILED DESCRIPTION OF THE INVENTION

Figure 1:
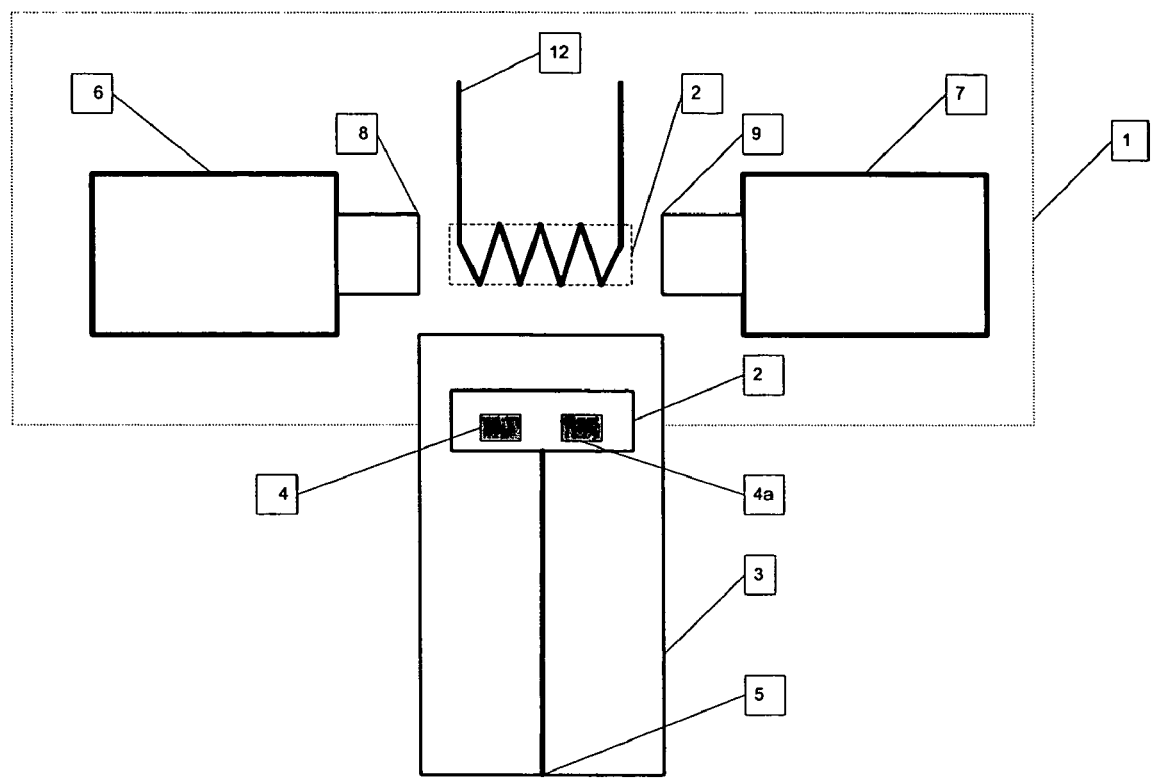
FIG. 1 is a schematic diagram of an apparatus embodying the invention.

For convenience, before further description of the present invention, certain terms employed in the specification, examples, and appended claims are collected here.

An "anti-clotting agent" refers to any molecule or compound that prevents the clotting of blood. Anti-clotting agents include, but are not limited to, anticoagulants, blood thinners, or drugs that prevent an overproduction of platelets.

The terms "apparatus" and "device" are used interchangeably herein.

A "clotting agent" refers to any molecule or compound that promotes the clotting of blood.

The term "coagulation" in the broadest sense refers to the process of changing from a liquid to a thickened, curdlike, state, not by evaporation, but by a chemical reaction. The term "coagulation" when referring to a blood sample refers to the process in which liquid blood is changed into a semisolid mass, e.g. a blood clot, through any of the clotting cascades or by a disturbance of hemostasis.

The term "coagulation state" of a sample refers to the degree of coagulation of a sample, e.g. completely liquid, completely coagulated, or at some point in between the beginning and end of the coagulation process.

The term "coagulation time" of a liquid refers to the time it takes

A "disturbance of hemostasis" refers to any interruption of blood flow in a vessel or to a body part.

"Ferromagnetic" materials have a large and positive susceptibility to an external magnetic field. They exhibit a strong attraction to magnetic fields and are able to retain their magnetic properties after the external field has been removed. Ferromagnetic materials have some unpaired electrons so their atoms have a net magnetic moment and derive their strong magnetic properties due to the presence of magnetic domains. In these domains, large numbers of atoms moments ($10^{12}$ to $10^{15}$) are aligned parallel so that the magnetic force within the domain is strong. When a ferromagnetic material is in the unmagnetized state, the domains are nearly randomly organized and the net magnetic field for the part as a whole is zero. When a magnetizing force is applied, the domains become aligned to produce a strong magnetic field within the part. Iron, nickel, gadolinium, cobalt, and alloys comprising these metals, such as alnicol and steel, are examples of ferromagnetic materials.

A "magnetic material" refers to any material that has a susceptibility to a magnetic field. Such materials are also referred to herein as "material which experiences a force when placed in a magnetic field".

"Paramagnetic" materials refer to those materials which have a small and positive susceptibility to magnetic fields. These materials are slightly attracted by a magnetic field and the material does not retain the magnetic properties when the external field is removed. Paramagnetic properties are due to the presence of some unpaired electrons and from the realignment of the electron orbits caused by the external magnetic field. Exemplary paramagnetic materials include the molecules magnesium, molybdenum, lithium, platinum, aluminum, and tantalum, and compounds such as olivine $(Mg, Fe)_2SiO_4$.

A "sample" includes material obtained from a subject. For example, samples may be obtained from a human or animal subject (including saliva, urine, blood), a plant, a cell culture or an environmental location, such as a water or an air sample. Sample also includes materials that have been processed or mixed with other materials. For example, a blood sample may be processed to obtain plasma, serum, red blood cells, etc., each of which may be considered a sample.

"Superparamagnetic" materials have individual domains of elements that have ferromagnetic properties in bulk, for example, such as a magnetic cluster ($Fe_2O_3/SiO_2$) within a non magnetic host (silica). Their magnetic susceptibility is between that of ferromagnetic and paramagnetic materials, defined above. Examples of superparamagnetic materials include, but are not limited to, iron containing contrast agents, such as iron oxide MION, and iron oxide nanoparticles, and $CoFe_2O_4$ nanoparticles.

The term "viscosity" refers to a substance's, particularly a liquid's, resistance to flow. Viscosity is a physical property of a substance that depends on the friction and/or molecular cohesion of its component molecules as they slide past one another in the substance. As a substance coagulates, its viscosity generally increases.

According to a first aspect of the present invention there is provided a method of determining the coagulation state of a liquid sample comprising the steps of: providing a sample of liquid containing at least one particle comprising a material which experiences a force when placed in a magnetic field; applying a magnetic field to the sample; using a magnetic field sensor to detect the movement and/or position of the at least one particle, thereby to determine the coagulation state of the sample.

According to a second aspect of the present invention there is provided the use of at least one magnetic field sensor to detect the movement and/or position of at least one particle within a liquid sample in order to determine the coagulation state of a sample, the particle comprising a material which experiences a force when placed in a magnetic field.

According to a third aspect of the present invention there is provided a device for determining the coagulation state of a liquid sample. In certain embodiments, a device comprises a region for receiving a liquid sample to be analysed; at least one particle disposed within said region the at least one particle comprising a material which experiences a force when placed in a magnetic field, means for applying a magnetic field to at least part of the region and at least one magnetic field sensor operative to detect movement and/or position of the at least one particle, whereby the coagulation state of the sample is determined.

The sample may comprise any liquid, for example, a biological fluid. All biological fluids, for example, blood, plasma, cerebrospinal fluid, urine, lymphatic fluid, semen, mucous, etc., have a viscosity that may be correlated with a disease state or condition. For example, the coagulation state or coagulation time of blood (which results in a change of viscosity of the blood) may be used to evaluate a degree of disturbance of hemostasis in the patient. For example, the sample may be blood or plasma where coagulation due to clotting or another disturbance of hemostasis is to be measured. Other disturbances of hemostasis measurable by the methods and devices of the invention include, but are not limited to, degree of platelet aggregation (e.g., by measuring the response to ADP, arachidonic acid, calcium ionophore, or collagen), the rate or amount of clot formation and/or clot dissolution, the time required for forming a fibrin clot, the protein C activation time (PCAT), kaolin clotting time, Russell's viper venom time (RVVT), and coagulation factor assays, such as those for fibrinogen activity (Clauss method) and concentration (ELISA antigenic determination), Factor II, Factor VII, Factor VIII, Factor IX, Factor X, Factor XI, Factor XII, prekallikrein, and high molecular weight kininogen. Further, hematocrit (red blood cell count) may be able to be determined from the viscosity of a blood sample. Still further, the potential for or degree of hyperviscosity in athletes may be monitored using the methods and devices of the present invention.

According to another aspect of the invention there is provided an apparatus for determining the coagulation time of blood or plasma, the apparatus comprising a container and a magnetic device, the container defining a chamber for holding a quantity of said blood or plasma, and the chamber holding particulate material, and the magnetic device co-operating with said container and being arranged in use to provide a magnetic field which causes the particulate material to migrate to and fro within the chamber through uncoagulated blood or plasma.

According to a further aspect of the invention there is provided a method of determining the coagulation time of blood or plasma, the method comprising the steps of causing particles of material which experiences a force when placed in a magnetic field to move through said blood or plasma; and noting as said coagulation time an instant at which changes in the properties of said blood or plasma at least reduce said movement In any of the above aspects and embodiments, the movement of said particles may be a to and fro movement.

The method may comprise cyclically providing a first and a second magnetic field, wherein said first magnetic field is provided from a first spatial location to cause said particles to translate in a first sense and said second magnetic field is provided from a second spatial location to cause said particles to translate in a second sense.

The strength of the provided magnetic fields may be between about 1 and about 100 milliteslas (mT). In certain embodiments, the magnetic field is between about 10 and about 50 mT, and in other embodiments it is in the range of about 10 to about 20 mT. The on time of each magnet may be less than 1 second.

The use of a magnetic field sensor as opposed to the use of light provides increased freedom as to the choice of material in which the liquid is contained. As a result of particles undergoing a migration to and fro through the liquid, assessment of the properties of the liquid is not confined to a narrow band as is the case in some prior devices.

The chamber may be of any suitable volume. In an embodiment the chamber has a volume of less than about 25 µl. In another embodiment the chamber has a volume less than about 5 µl. The chamber may be of any convenient shape. In an embodiment the chamber is formed in a disposable support strip which is removable from the device. Fluid may be introduced into the chamber by any convenient means, including capillarity. The chamber may be of any suitable material that enables the test to be performed and may be constructed of a non-magnetic material.

In an embodiment a filling device for filling the container includes a capillary. In another, the filling device includes a plunger. The device may comprise more than one chamber. The chamber may be divided into two, three or more compartments.

In one embodiment the material which experiences a force when placed in a magnetic field, or respectively the particulate material, is ferromagnetic. In another it is paramagnetic. In yet another it is superparamagnetic.

In certain embodiments, the particles may be generally spherical. In certain embodiments, the particles have a size in the range of about 2 to about 500 µm, and, in other embodiments, a size in the range of about 2 to about 20 µm in at least one direction. Particles may comprise two or more different materials and only one material need experience a force when exposed to a magnetic field.

In another embodiment the particles may be elongated or symmetrical in nature.

In certain embodiments, a plurality of particles are used.

The particle or particles must be of a sufficient quantity and/or size as to allow for their movement in a non-coagulated fluid sample.

The quantity and/or mass of the particles in each test-strip or within each chamber or compartment of a particular test-strip may be known prior to measurement. Alternatively, the quantity and/or mass may be compensated for by the initial measurement of the uncoagulated sample.

In certain embodiments, the device may comprise at least one reagent disposed within a chamber prior to introduction of a sample to be analysed. The methods may further comprise the use of reagents to inhibit changes in viscosity of a sample so that it does not change its viscosity within the time frame of the test (so that an accurate assessment of its state in the subject from it is drawn may be made), or use of reagents to speed up a change in viscosity of the sample, if required. The methods may also comprise the use of reagents suitable for measurement of a particular disease or condition associated with the viscosity of a particular biological fluid sample. Multiple reagents may be used in the subject methods such as to be able to alter the change in viscosity and/or times of viscosity change.

For example, the methods may in some embodiments further comprise the use of reagents to inhibit the clotting of the sample so that it does not clot within the time frame of the test, or use of reagents to speed the clotting of the sample, if required. The methods may also comprise the use of reagents suitable for measurement of a particular disturbance of hemostasis. Multiple reagents may be used in the subject methods such as to be able to alter the clotting rate and/or times.

For example, such reagents may be anti-clotting agents used to inhibit the clotting of the sample so that it does not clot within the time frame of the test. Alternatively, such reagents may be clotting agents used to speed the clotting of the sample, if required. Where more than one chamber or compartment is employed, the reagents disposed in each may be different such as to be able to alter the clotting rate and/or times. Alternatively, one of the compartments or chambers may have no reagent present such that the clotting time independent of a reagent may additionally be measured.

Any anti-clotting agent, such as an anticoagulant, blood thinner, or drug that prevents an overproduction of platelets may be used with the devices of the invention. Non-limiting examples of anti-clotting agents are aspirin, heparin (standard, or unfractionated, or low-molecular weight heparin (LMWH), including enoxaparin, dalteparin, and tinzaparin), warfarin, thienopyrindines such as ticlopidine and clopidogrel, dipyridamole, glycoprotein IIb/IIIa receptor antagonists (such as abciximab, eptifibatide, lamifiban, and tirofiban), argatroban, danaproid, and lepirudin.

Non-limiting examples of clotting agents are: thrombin, calcium ions, coagulation factor VII, factor VIII, factor XIII, factor IX, moroctocog alpha (Factor VIII without B domain), chitosan, antifibrinolytic amino acids (such as aminocaproic acid and tranexamic acid), aprotinin, desmopressin, conjugated estrogens, and plasminogen activators.

In other embodiments, the reagents may be reagents suitable for measurement of a particular disturbance of hemostasis, such as the prothrombin time (PT) test. Other reagents may be used to aid in the measurement of the degree of platelet aggregation, the rate or amount of clot formation and/or clot dissolution, the time required for forming a fibrin clot, the activated partial thromboplastin time (APTT), the activated clotting time (ACT), the protein C activation time (PCAT), the Russell's viper venom time (RVVT) and the thrombin time (TT).

For example, suitable reagents for measurement of PT include, Thromborel S™ and Innovin™ (produced by Dade) and ThromboTest™ (produced by Axis Shield). The PT test The test is performed by adding such clotting agents to a patient sample and then measuring the coagulation time. This test could be practiced, for example, using embodiments of the present invention wherein time of coagulation is measured using the methods and/or after clotting agents are added to a sample, or in which clotting agents are already present in the sample chamber or released into the sample chamber when the sample is added. Such methods or devices may express the PT using the Internationalized Normalized Ratio or INR, discussed above.

Another method of measurement of coagulation in either blood or plasma is the Activated Partial Thromboplastin Time Test (APTT). This test is a measure of the time of coagulation that occurs when the intrinsic pathway is activated. This is achieved by the addition of an activator (kaolin) to the sample in the presence of calcium ions and phospholipid (partial thromboplastin). This test could be practiced, for example, using embodiments of the present invention which measure time of coagulation after reagents are used to activate the pathway in a sample. Such reagents may be added to the sample before the method is performed or before it is added to a device, or such reagents may be already present in the sample chamber or released into the sample chamber when the sample is added.

The Activated Clotting Time Test (ACT) resembles the APTT test and is used to monitor a patient's blood coagulation status during procedures that involve the dosing of high amounts of heparin, such as percutaneous transluminal coronary angioplasty (PCTA) and cardiopulmonary bypass surgery. This test could be practiced, for example, using embodiments of the present invention which measure coagulation state.

The Thrombin Time Test (TT) measures the rate of formation of a fibrin clot in plasma by the action of thrombin on fibrinogen, compared to a normal plasma control. The test is performed by adding a standard amount of thrombin to a patient's plasma that has been deprived of platelets and measuring the time for a clot to form. This test could be practiced, for example, using embodiments of the present invention which measure time of coagulation after thrombin is added to a sample.

The reagents may be initially disposed in any suitable place within the interior sample region of the test-strip and may be disposed there prior to introduction of a fluid sample to be analysed. In some embodiments, the sample region is a chamber or plurality of chambers. For example the reagents may be disposed in a sample chamber or chambers or in separate chambers and/or compartments. As an alternative, the magnetic particles and/or clotting reagents may be mixed with the sample prior to addition to the strip.

A single detector or pair of detectors may be employed for determining the clotting time of sample present in more than one chamber or compartment. In this case the detector or detectors measure the sum total of the magnetic field strength of the particles in each of the chambers or compartments. Where this is the case, the quantity and/or mass of particles and/or reagents present in each of the chambers or compartments should be chosen such that the reader is able to establish which chamber or compartment has clotted.

Alternatively a single detector or pair of detectors may be employed for determining the clotting time of sample present in each chamber or compartment.

The applied magnetic field may be kept at a constant value during the measurement or it may be caused to vary.

The time of application of the magnetic field may be kept at a constant value during measurement or it may be caused to vary In a described embodiment, plural particles are disposed in the chamber prior to introduction of a sample of liquid. In the described embodiment, the particles are secured with respect to an inner wall of the chamber, and arranged to enter into suspension in a sample when the sample is introduced into the chamber. In one embodiment the particles are distributed on walls of the chamber as a dry coating.

The means for providing a magnetic field may comprise two spaced apart electromagnets. The electromagnets may be disposed on mutually opposite sides of the chamber. Alternatively they may be disposed on the same side of the chamber. Each electromagnet may be a solenoid. The solenoids may be substantially coaxial.

In one described embodiment, the magnets are activated alternately with a direct current, to produce a constant field. The magnitude of field produced by one magnet may be greater than the other.

At least one magnetic field sensor may be a Hall Effect sensor. In the described embodiment two or more sensors are provided, each one associated with a respective magnet. In operation the magnetic field measured by a sensor will, amongst other things, be affected by the position of the at least one particle relative to the sensor. Thus, the output of a sensor can be used to determine position and/or movement of the at least one particle in the chamber.

Where two sensors are used in a differential measurement, an increase in sensitivity is created with a reduction in noise. Any external effects are detected by both sensors simultaneously and hence are cancelled out. The device therefore reads only the changes in the sample.

In the described embodiment two sensors are disposed near opposite ends of an elongate chamber each between the chamber and a respective magnet. When analysing a sample of liquid in the chamber each magnet is alternately activated. After each magnetic is activated a period is allowed for each particle to migrate across the chamber. Then, a series of measurements of the differential output of the sensors is taken and a mean value calculated. The other magnet is then activated and the process repeated.

The device may include circuitry for measuring the time elapsed from introduction of a sample until coagulation is detected. The device may comprise a control means, which may comprise a microprocessor. The device may comprise a display, operative to display information to a user. For example, in embodiments wherein the coagulation state or time of a blood or plasma sample is measured, the device may display a clotting time and/or an INR value.

The device may comprise means for heating the chamber, to maintain a sample being analysed at a desired temperature.

EXEMPLIFICATION

The invention having been generally described, may be more readily understood by reference to the following examples, which are included merely for purposes of illustration of certain aspects and embodiments of the present invention, and are not intended to limit the invention in any way.

Example 1

Apparatus for Analyzing Coagulation

The apparatus of FIG. 1 comprises a measurement unit 1 and a separate sample chamber 2 which, in use, is inserted into the measurement unit 1.

In this embodiment, the sample chamber 2 is defined within a slide-like structure hereinafter referred to as a strip 3 (see FIG. 12). The material of the structure which defines the chamber 2 is non-magnetic, and the chamber has a volume of about 1 μl. The chamber 2 contains a known quantity number of superparamagnetic particles 4 and a dry reagent for blood clotting 4a distributed about the internal surface of the chamber 2. A suitable clotting agent is recombinant human tissue factor (Innovin®). The superparamagnetic particles 4 in this embodiment are substantially spherical and have an average diameter of about 10 μm. A capillary 5 extends from a point on the strip 3 remote from the chamber 2 into the chamber 2. In use, a sample of blood placed at sample-receiving opening 105 of the capillary 5 flows along the capillary, under capillary action, into the chamber 2.

Figure 2:
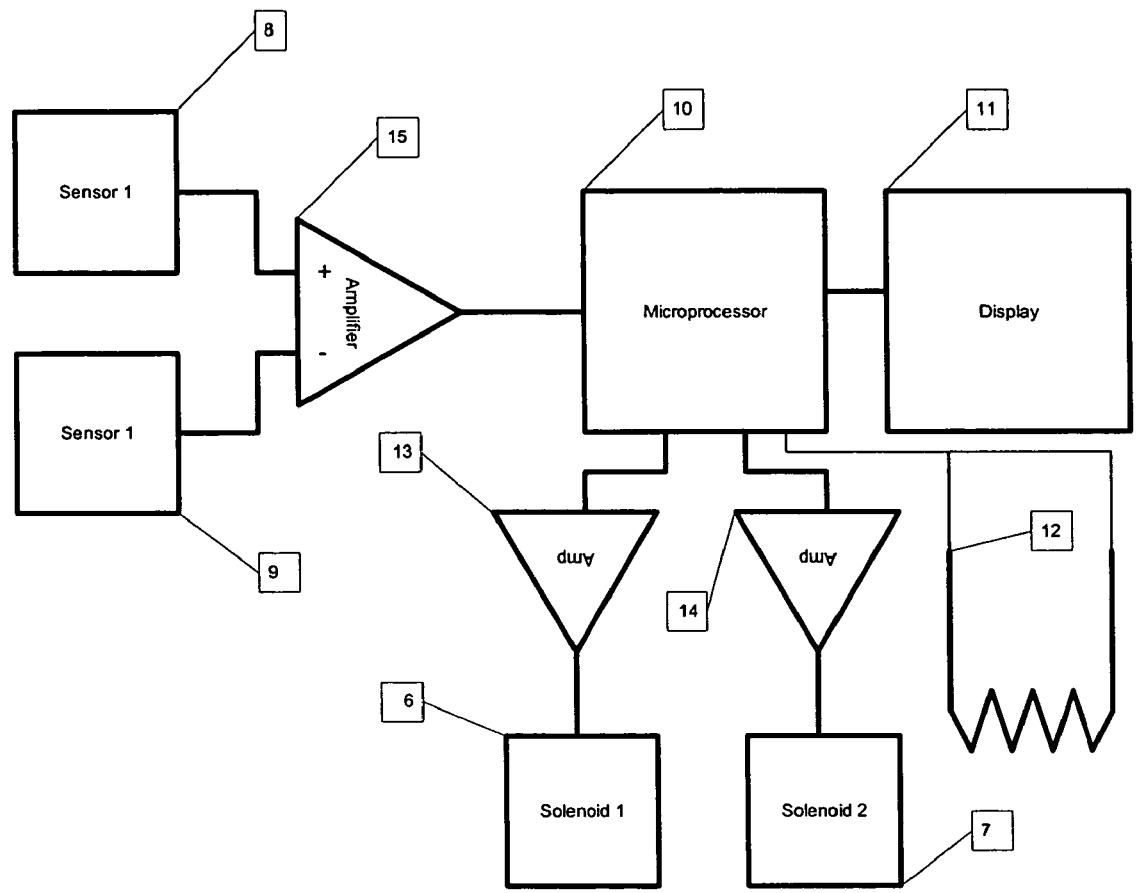
FIG. 2 is a block circuit diagram of the apparatus of FIG. 1.

The measurement unit 1 comprises first and second spaced apart substantially coaxial solenoids 6, 7. The first solenoid 6 supports a first Hall Effect sensor 8 on a surface thereof directed towards the second solenoid 7. The second solenoid 7 supports a second Hall Effect sensor 9 on a surface thereof directed towards the first solenoid 6. The Hall Effect sensors 8, 9 are coaxial with the solenoids 6, 7. The measurement unit 1 also includes various associated electrical circuitry (see especially FIG. 2) including a microprocessor 10. The unit also comprises a power supply (not shown), display 11 and a resistive heating element 12 for heating a sample to be analysed.

Figure 12:
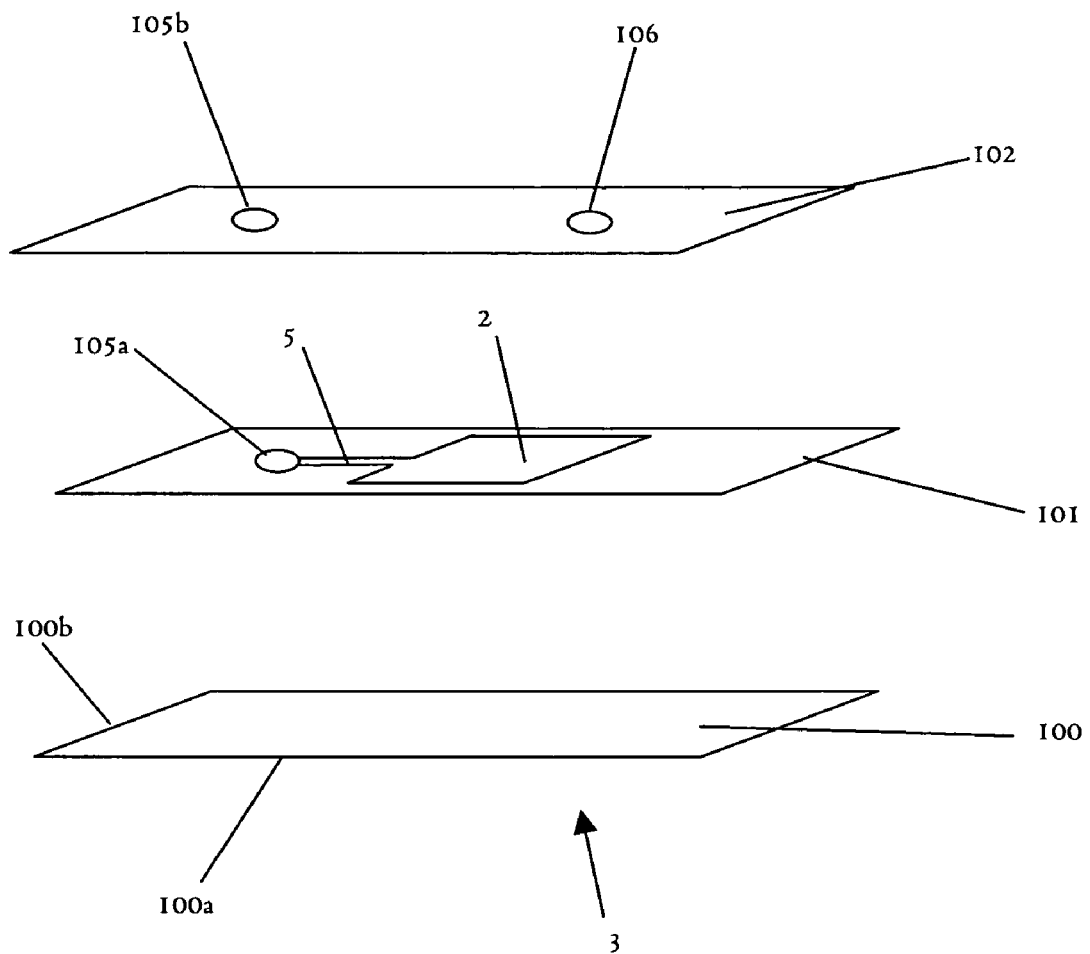
FIG. 12 shows a perspective exploded view of a sample chamber structure.

Referring now to FIG. 12, the strip 3 of this example has three layers 100-2, the material of which is selected according to the application concerned. Since embodiments of the invention do not require any particular optical properties, the materials can be freely selected bearing in mind of course that non-magnetic materials are needed. For example, there is no need to use glass where glass or particular types of glass are undesirable. The first layer 100 is a substrate here of polymeric material, and is a generally rectangular plate with, in this example, a length 100a about four times its width 100b. The second layer 101 is of like material, and outer dimensions. Internally it defines a generally rectangular opening 2 which forms the chamber 2, and which extends over most of the width of the layer 101. The capillary 5 is formed by a relatively narrow channel communicating with one end of the opening 2 and extending to a circular aperture 105a forming part of the sample receiving opening. The third layer 102 is of like size to the other layers and has first and second circular apertures 105b and 106. When the three layers are cemented together, the first aperture 105b of the third layer registers with the circular aperture 105a of the second layer. The second aperture 106 then lies over the opening 2 to form a vent.

The unit 1 has a support, not shown, for the strip 3 so that when a strip 3 is engaged by the support the chamber 2 lies between and substantially on the axis of the solenoids 6, 7. In this disposition the first and second Hall Effect magnetic field sensors 8, 9 lie in close proximity to both the chamber 2 and its associated solenoid 6, 7, contacting the chamber 2. In another embodiment, there is a small space between the sensors 6, 7 and the chamber 2.

The resistive heating element 12 is also located so that it is associated with the chamber 2 when the strip 3 is inserted into the unit 1, so that it is operative to heat a sample in the chamber 2.

In an alternative embodiment, no resistive heating element is provided. Instead, any necessary heating of a sample in the chamber 2 is achieved by driving one or both solenoids 6,7 with a high frequency alternating current to generate an alternating magnetic field and cause inductive heating of the superparamagnetic particles 4 in the chamber 2 and thereby heat any sample in the chamber 2.

The microprocessor 10 is operative, amongst other things, to control supply of current to the two solenoids 6, 7 by means a respective amplifier 13, 14 for each solenoid.

The two Hall Effect sensors 8, 9 are connected to a differential amplifier 15 which supplies the differential output of the sensors to the microprocessor via ADC circuitry (not shown).

In use a user switches on the unit and inserts the strip 3 into the unit 1, so that the chamber 2 is positioned between the solenoids 6, 7.

If necessary, the microprocessor 10 causes the chamber 2 to be heated to a temperature of about 37° C. In this embodiment, the microprocessor has a further connection to one or both the Hall Effect sensors 8,9 for measuring the resistance thereof to measure the temperature of the chamber. Other techniques are of course possible, including measurement of the resistance of the heating element 12, or provision of a separate thermal sensor.

In other embodiments, heating of the chamber to 37° C. is not necessary. Other, e.g. lower, temperatures can be used since with knowledge of the temperature of the sample the times determined by apparatus of the invention can be corrected to the values that would be achieved if the standard 37° C. were used. In one embodiment, no heating is used, and the temperature measured, e.g. by a sensor, and the necessary corrections applied.

Figure 3:
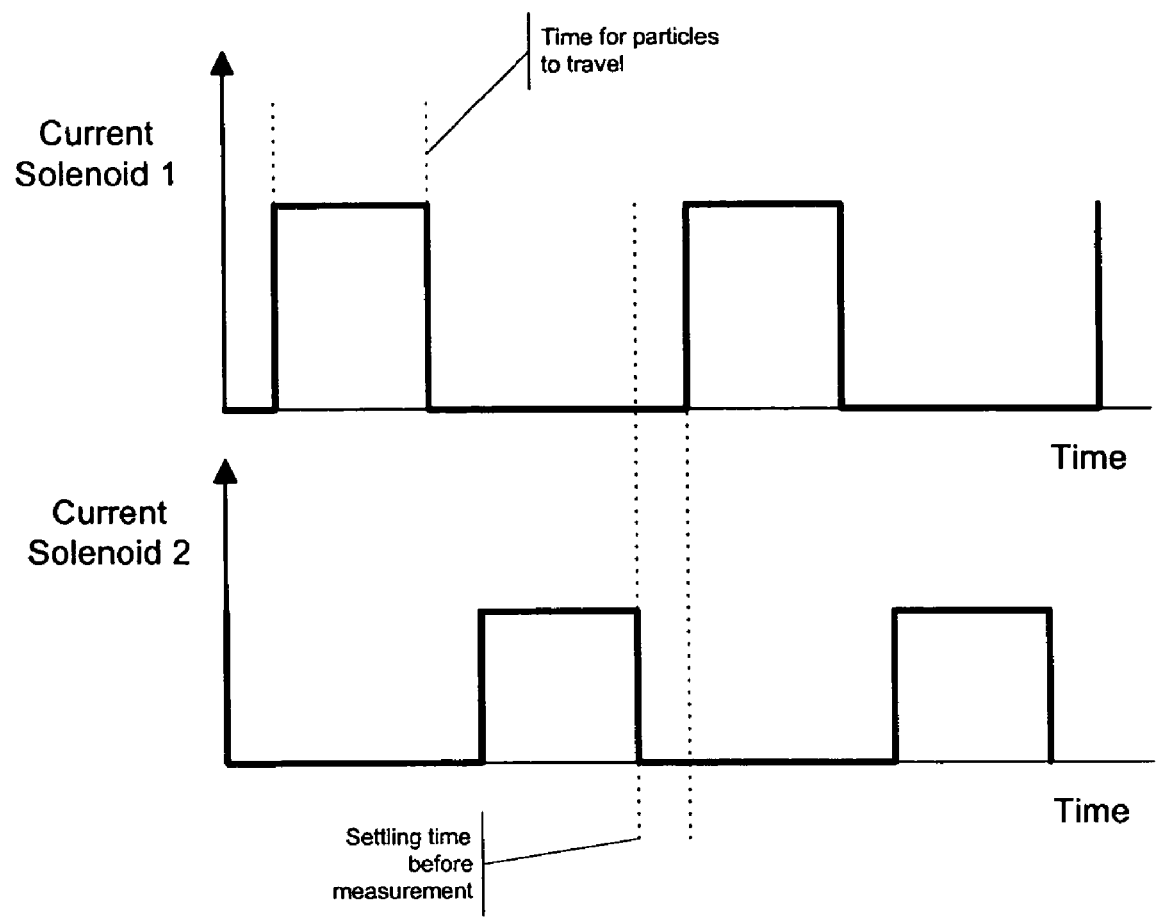
FIG. 3 is a graph plotting current against time for the solenoids of the apparatus of FIG. 1 when establishing baseline field values.

On insertion of the strip 3, the apparatus is programmed to takes baseline magnetic field measurements, thereafter to enter a "wait" state and finally to carry out a measurement cycle. To initiate the baseline measurements, the strip 3 operates a switch (not shown) which actuates the microprocessor 10 to cause a direct current of a first magnitude to flow in the first solenoid 6. After a predetermined time of about 200 μs has passed to allow the magnetic field produced to form and settle the differential output of the Hall effect sensors 8,9 is measured sequentially a predetermined number, about 500, times over a predetermined period of about 800 μs during which the magnetic field produced by the solenoid 6 remains substantially constant. These measurements are stored and a mean value determined. The mean value is then stored as a baseline value for the first solenoid 6 (B1). The current flowing in the first solenoid 6 is then stopped and the process is repeated for the second solenoid 7, save that the current used is of a second magnitude, smaller than the first. This establishes a baseline value for the second solenoid 7 (B2). A graph of the current applied to each solenoid 6, 7 is shown in FIG. 3. Once the baseline values B1 and B2 have been recorded and stored one of the solenoids 6, 7 remains activated and the apparatus is ready to receive a sample of blood. An indicator (not shown) informs the user of this. The indicator may be a light, such as an LED, or a buzzer or any other appropriate indicator. Alternatively, a barrier, such as a gate, may be provided to prevent access to the capillary 5, and the barrier moved or unlocked once the apparatus is ready for use.

When a user places a blood sample on the end of the capillary 5 on the strip 3, the blood then flows into the chamber 2. On entering the chamber 2 the blood reacts with the clotting reagent 4a. The blood also frees the superparamagnetic particles 4 which can then move in suspension in the blood.

The presence of blood in the chamber 2 allows the particles to come into suspension. This then causes an increase in the differential output of the Hall Effect sensors 8,9 at the output of the differential amplifier 15. The differential output changes in the main because the superparamagnetic particles 4 move towards whichever solenoid 6,7 is activated, and hence its associated Hall effect sensor 8,9, affecting the magnetic field experienced by both sensors in opposing senses. A minor effect is caused by the inherent properties of the blood.

Figure 4:
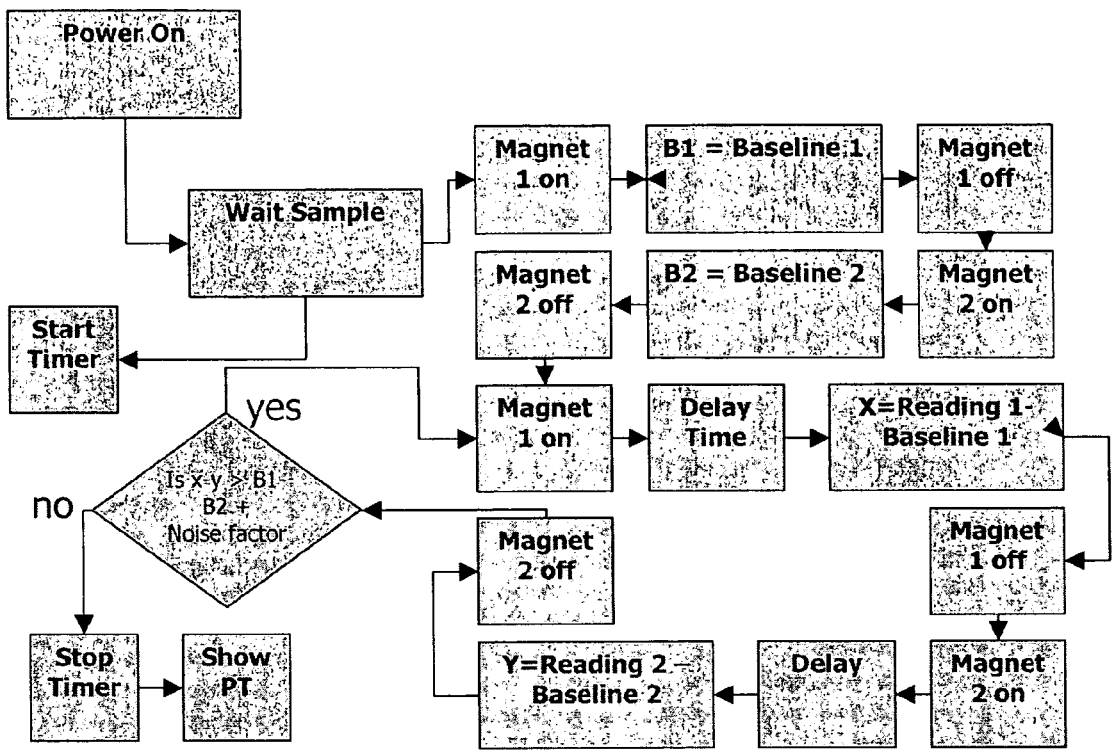
FIG. 4 is a flow chart of the operation of the apparatus of FIG. 1.

The microprocessor 10 detects the increase in output and in response thereto starts a timer to begin a measurement sequence. During this sequence the microprocessor alternately energises the solenoids 6, 7 in a non-overlapping fashion and records the average output of the differential amplifier 15 using the same sequence of operation as when measuring B1 and B2. For each cycle of operation the microprocessor 10 determines if the difference between the sequential average outputs of the differential amplifier 15, measured when the first 6 and second 7 solenoids are activated, is greater than B1-B2 plus a noise factor. When this condition is met it indicates that the sample has clotted. The timer is stopped. The time elapsed recorded by the clock is the coagulation time for the sample, from which with a knowledge of the clotting agent in the chamber 2, an INR value is calculated by the microprocessor. FIG. 4 is a flow chart showing the operation of the apparatus following introduction of a strip 3.

In other embodiments, a different analysis of the output of the Hall sensors is performed, for example the rate of change of output is measured. In embodiments where only one Hall sensor is provided, different arrangements are possible. In one, comparison of the current output with an original output is performed and indication of clotting is given when the difference exceeds a set threshold. In another, the rate of change of output is determined.

Figure 5:
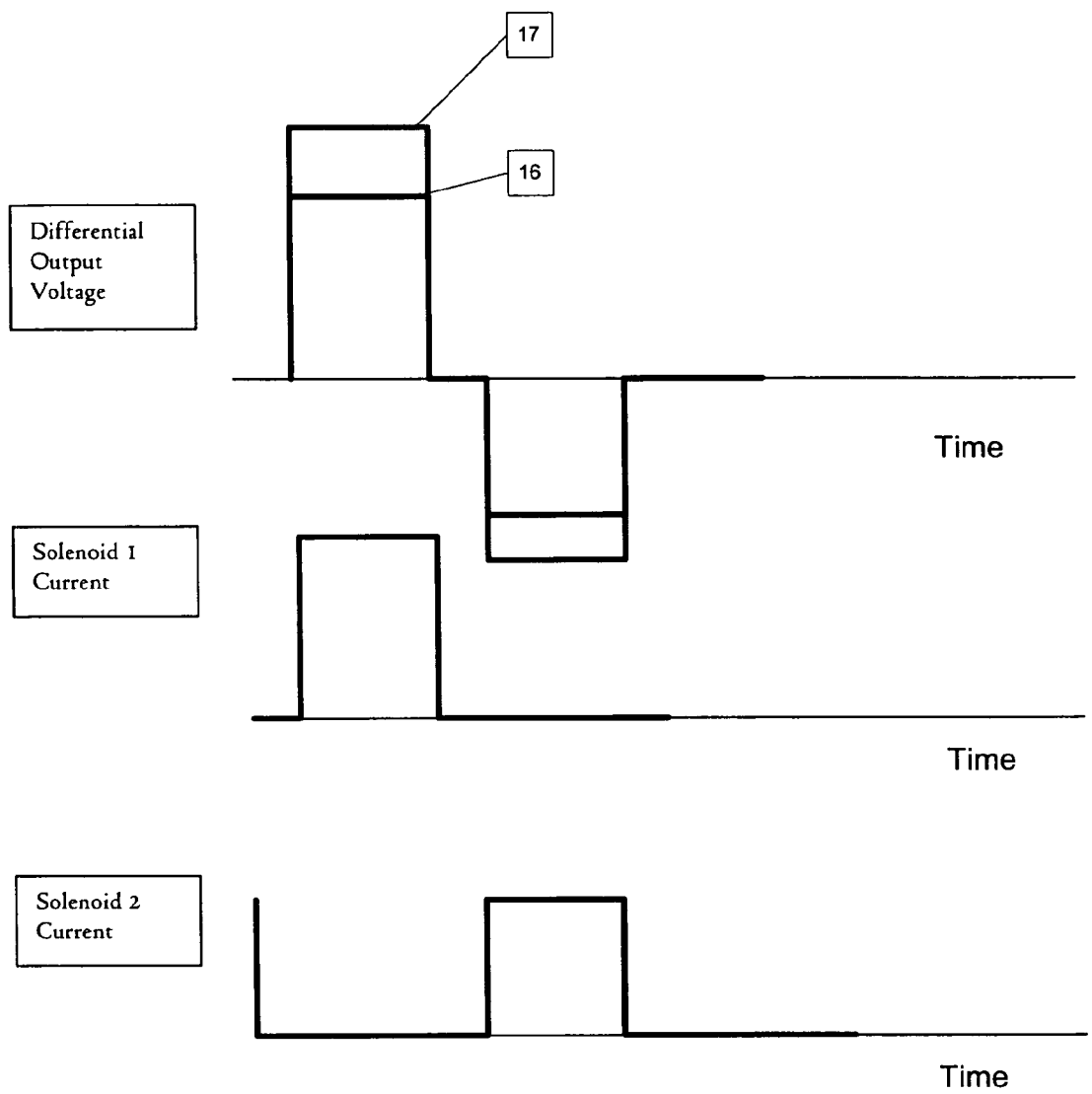
FIG. 5 is a graph plotting current against time for the solenoids of the apparatus of FIG. 1 together with typical detector output.

To explain operation in further detail, FIG. 5 shows a single cycle of the current which flows in each solenoid 6,7 during the determination of the baseline, and measurement sequence, together with typical differential output of the Hall effect sensors 8,9 both when determining the baseline 11 and when a blood sample has been introduced 17 into the chamber 2.

During the measurement sequence each solenoid 6,7 is energised for a sufficient time to enable the superparamagnetic particles 4 to travel from one end of the chamber 2 to the other, at least when a fresh sample of blood is first introduced into the chamber 2.

As the blood in the chamber 2 clots movement of the superparamagnetic particles 4 through the blood becomes progressively restricted. For the blood sample selected and with the appropriate selection of magnetic field a time is reached where the particles 4 will only move under the influence of the field produced by the first solenoid 6, which as greater than that of the second solenoid 7 by virtue of the greater current with which it is supplied. Consequently the particles 4 will accumulate and remain at the end of the chamber 2 closest to the first solenoid 6.

It will be understood that the condition of non-moving particles is specific to this embodiment; in other testing arrangements or with other blood samples some particles may continue to move.

The location of the particles 4 in the chamber 2 affects the differential output of the Hall Effect sensors 8,9. The change in the differential sensor output when the particles 4 stop moving through the blood sample and remain towards one end of the chamber 2 serves as an indication that the blood has clotted.

Figure 6:
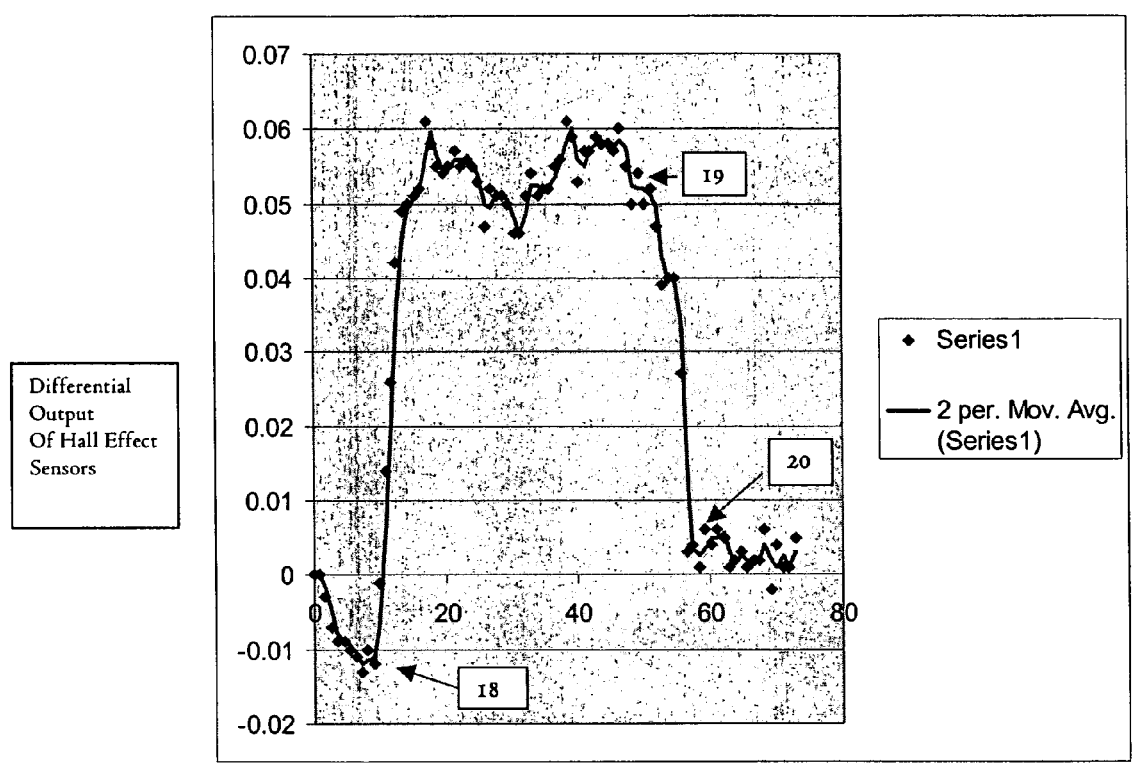
FIG. 6 is a graph plotting differential sensor output against time for a sample of blood.

FIG. 6 shows the average differential output of the Hall effect sensors 8,9 when the first solenoid 6 is energized (less B1—in order to show the true effect of the superparamagnetic particles 4 in the sample) less than when the second solenoid 7 is energized (less B2) over time during analysis of a sample of blood.

Initially, no blood is present in the chamber 2 and the value is low. Blood is introduced at 18 which causes the value to rise sharply. At this point the microprocessor 10 starts a timer. As a clot starts to form 19 the differential sensor output begins to fall, and then falls steeply and levels off as the clot completes 20. This sudden change in the differential output greatly facilitates determination as to when clotting has occurred, at which point the microprocessor 10 stops the timer. The timer then indicates the coagulation time. Once measurement has completed the strip 3 can be removed and discarded. A new strip is used for a future measurement.

The parameters of the measurement sequence can be varied depending upon the characteristics of a sample being analysed and the required accuracy. The measurement sequence discussed above involves a solenoid switching time of about one second. That is to say that each solenoid is activated for about one second in an alternating sequence. As the clotting time of a sample increases the switching time may also be increased whilst maintaining accuracy of the measured coagulation time. For example, if a 5% error is required for an INR of 1 at twenty seconds then a switching time of one second is suitable. If the same error is required for an INR of 8 at sixty seconds then a switching time of eight seconds is suitable. An advantage of a longer switching time is that the resultant movement of the superparamagnetic particles 4 is less destructive of clot formation which is useful where higher INRs are concerned since the clot formation is potentially weaker. Another advantage is that a higher switching time reduces the power requirements of the apparatus.

Figure 7:
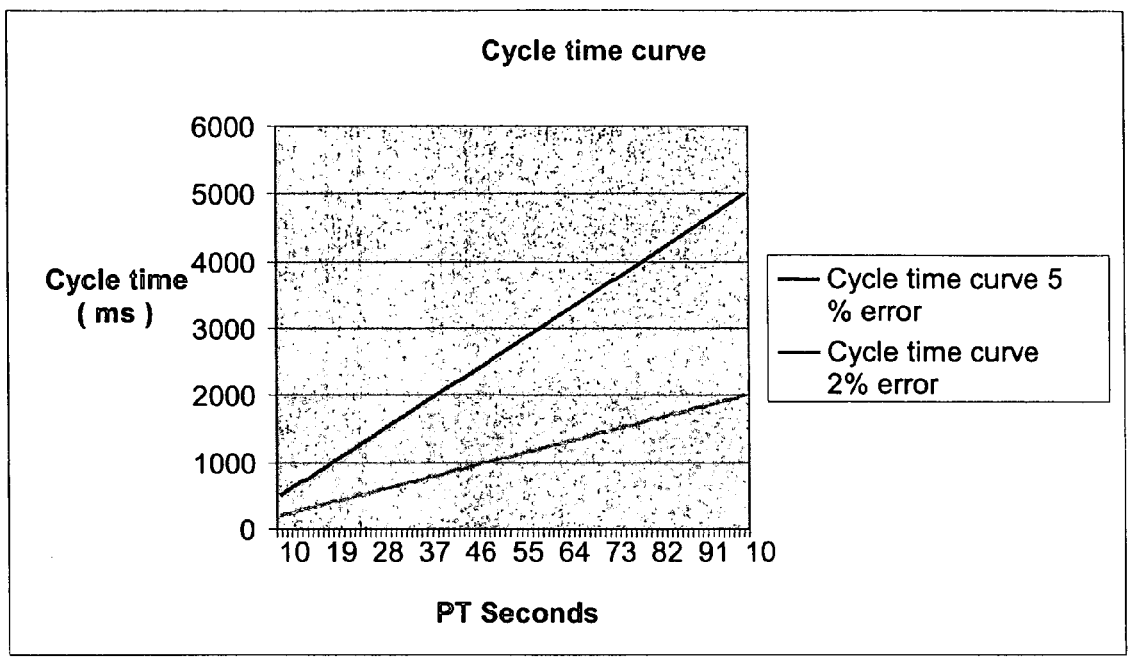
FIG. 7 is a graph plotting switching time against prothrombin time.

FIG. 7 illustrates example switching time curves for 2 and 5% errors for prothrombin times (PT) of between 10 and 100 seconds.

Where higher INRs occur, in one embodiment the magnetic field strength is reduced with time. This results in less disturbance of clot formation and reduces the power requirement of the apparatus. To achieve this, the embodiment maintains standard field strengths from the two solenoids up to a predetermined time threshold, and then progressively reduces the field strengths.

In addition to determining clotting time the apparatus can also measure the viscosity of a sample by measuring the time for the superparamagnetic particles 4 to travel across the known distance between opposite ends of the chamber 2.

Example 2

Use of the Apparatus of Example 1 to Analyze Coagulation Time in Blood

Fresh blood samples were obtained from a local hospital ranging from IRN 2.2 to 5.5 and one standard INR blood obtained by a healthy donor. The INR value for each blood sample was determined using an Amelung KC10A micro bench top coagulation meter with no hematocrit correction measured.

One of the samples was read after the experiment and treated as a blind test to see if the apparatus of the embodiment would give a value for INR when compared to the other known value.

A capillary tube (Camlab 200 μm tubes product number VD/3520-100 which were cut down to 25 mm) was placed into the measurement unit 1 in a controlled temperature environment (37° C.). For use in the experiment superparamagnetic particles 14 Liquid Research Limited code number PM002 particles or Polysciences Inc. catalogue number 19233 12μ range carboxylated paramagnetic particles were selected. The particles were weighed out and made up to a 3% weight per volume suspension in Innovin. (DADE BEHRING Innovin 10 ml bottle dissolved in 5 ml of distilled water).

The 3% by weight suspension of particle and Innovin was mixed using a vortex mixer. A portion of the suspension (10 μl) was dispensed into an Eppendorf tube.

A blood sample (20 μl) was added to the Eppendorf tube. At the same time there were started both the data capture system on the computer of the measurement unit 1 and a hand held stopwatch. The sample was mixed on a vortex mixer and a portion of the blood sample (4 μl) was added to the end of the capillary tube.

The particles in the sample were visually observed. When the particles stopped moving the data collection system of the Hall Effect Jig observed the same response.

The remaining sample within the Eppendorf tube was mixed with the top of a pipette tip at the same time the measurement unit 1 was running the test. When the sample within the Eppendorf tube was seen to have clotted the stopwatch was stopped (see Table 1 below which shows the stopwatch times obtained by measuring the clotting time of the blood sample that remained in the Eppendorf tube.)

TABLE 1

| IRN | Rep | Stopwatch time | Comment |
|---|---|---|---|
| 1 | 1 | 17.4 | Blood spilt outside capillary |
| 1 | 2 | 16.9 | |
| 1 | 3 | 16.6 | |
| 1 | 4 | 17.1 | |
| 1 | 5 | 16.8 | Capillary moved when filling |
| 1 | 6 | 17.24 | |
| 1 | 7 | 15.6 | |
| 2.2 | 1 | 23 | |
| 2.2 | 2 | 25 | |
| 2.2 | 3 | | Small amount of blood outside capillary |

TABLE 1-continued

| IRN | Rep | Stopwatch time | Comment |
|---|---|---|---|
| 2.2 | 4 | 26.8 | |
| 2.2 | 5 | 24 | |
| 3.2 | 1 | 29.5 | |
| 3.2 | 2 | 29.8 | |
| 3.2 | 3 | 30.02 | |
| 3.2 | 4 | 31 | Capillary did not fill evenly |
| 3.2 | 5 | 28.9 | |
| 4.3 | 1 | 39.06 | |
| 4.3 | 2 | 42.5 | |
| 4.3 | 3 | 41.1 | |
| 4.3 | 4 | 41.5 | |
| 4.3 | 5 | 38.2 | |
| 4.3 | 6 | 38.75 | |
| 5.5 | 1 | 56.18 | |
| 5.5 | 2 | 57.1 | Particles bridging seen |
| 5.5 | 3 | 61.5 | |
| 5.5 | 4 | 58 | |
| 5.5 | 5 | 57.9 | |
| 5.5 | 6 | 57.2 | |
| 1B | 1 | 16.2 | |
| 1B | 2 | 17.2 | |
| 1B | 3 | 16.55 | |
| 1B | 4 | 18.12 | |
| 1B | 5 | 18.25 | |
| 1B | 6 | 16.2 | |
| X | 1 | 31 | Blind INR value |
| X | 2 | 28.1 | |
| X | 3 | 28 | |
| X | 4 | 27.1 | |
| X | 5 | 28.26 | |

Figure 10:
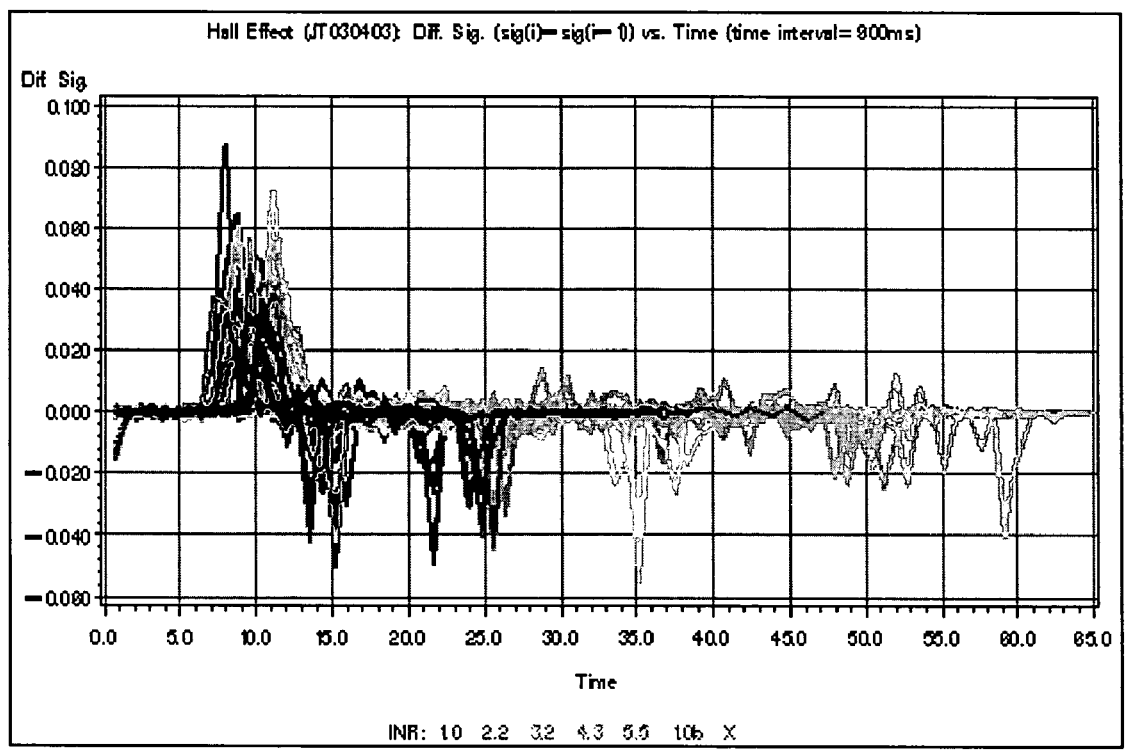
FIG. 10 is a graph plotting sensor output against time.

The readout from the Hall effect sensors 8,9 was displayed to show the change in signal against time—see FIG. 10. Clotting is indicated as the point at which the signal changes at the negative peaks.

Figure 11:
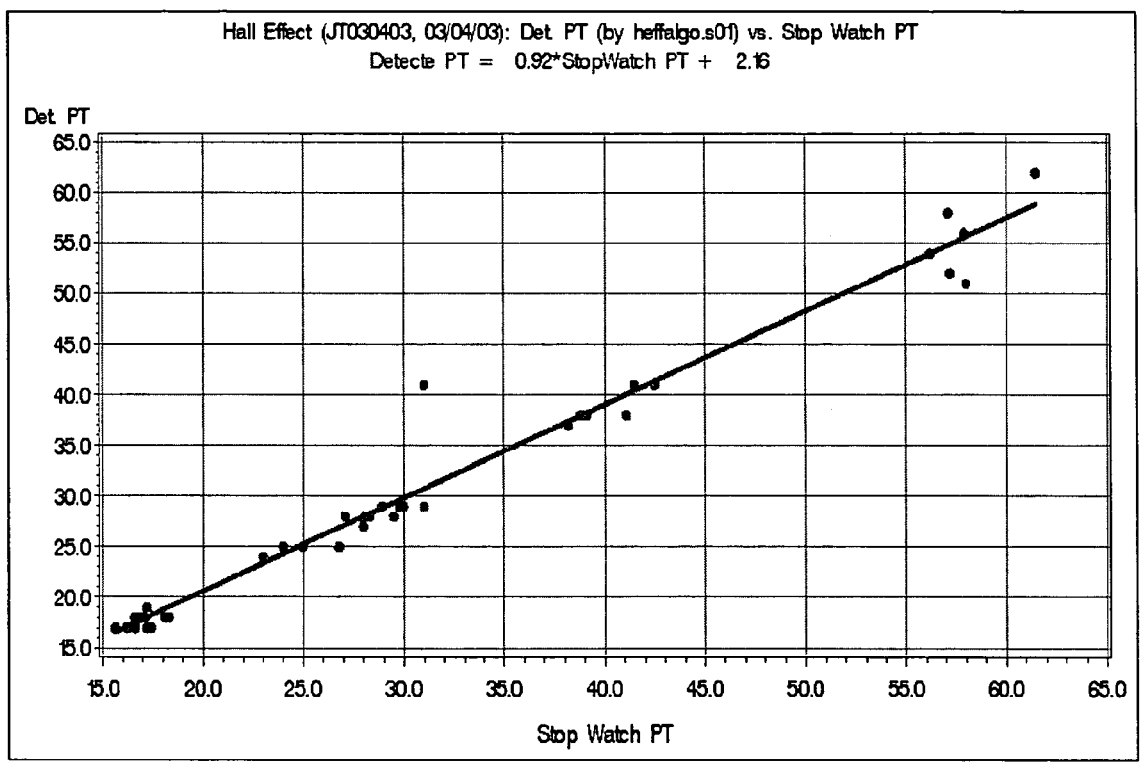
FIG. 11 is a plot showing coagulation times achieved using an apparatus of the invention against coagulation times derived from a visual method.

The data obtained from signal change from the measurement unit 1 was compared with the stopwatch data. The result of the comparison is shown in FIG. 11.

Figure 8:
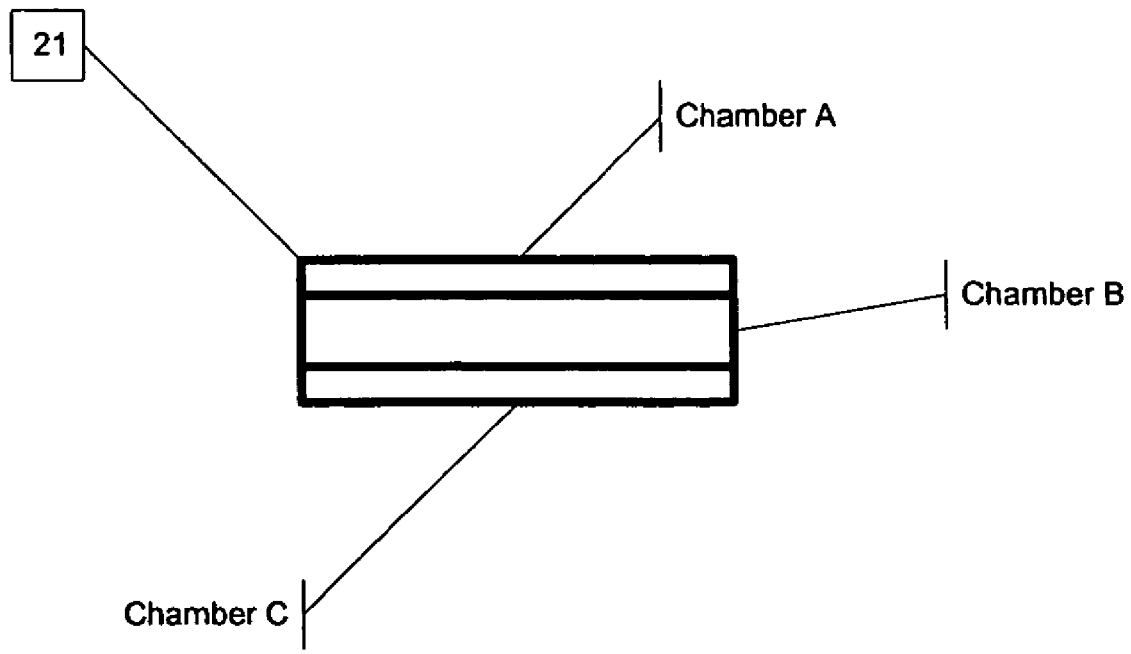
FIG. 8 is a schematic diagram of an alternative chamber for use with the apparatus of FIG. 1.
Figure 9:
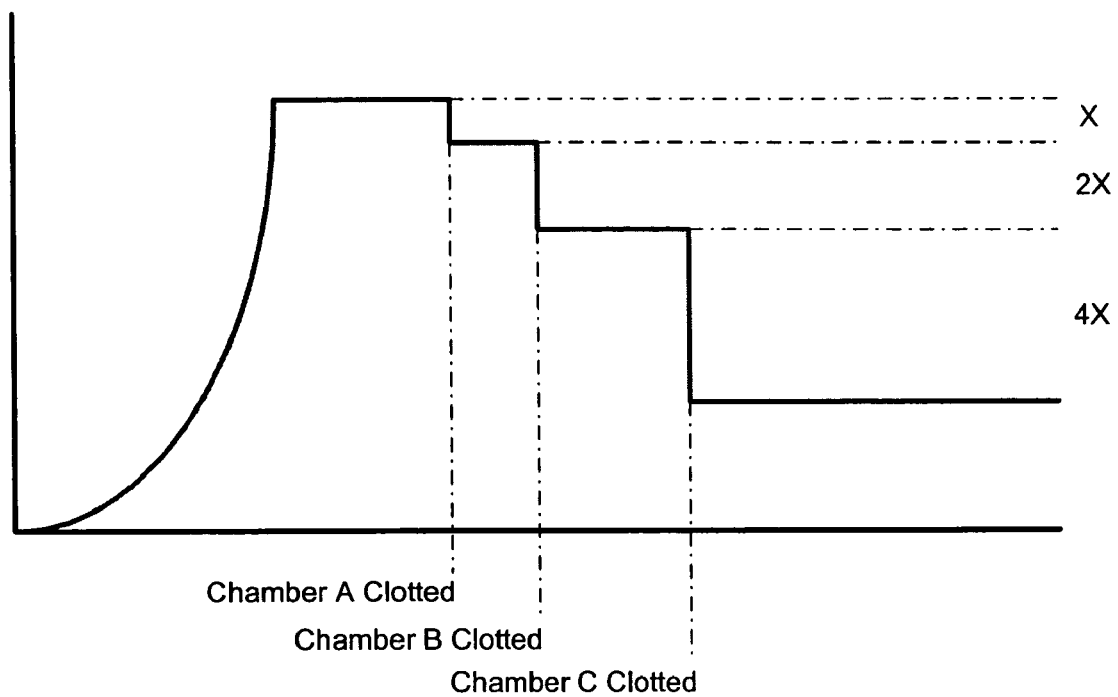
FIG. 9 is a graph of detector output against time for a sample of blood in the chamber of FIG. 8.

Referring to FIGS. 8 and 9 one embodiment of the apparatus is self-calibrating. To achieve this, there is employed a chamber 21 with three or more separate compartments each internally coated with a different proportion of clotting agent and containing a different quantity of superparamagnetic particles 4. The chamber 2 comprises three separate compartments, A, B and C. Compartment A contains a quantity X of superparamagnetic particles 4 and a reagent with a known short clotting time for any type of blood. Compartment B contains 2X superparamagnetic particles 4 and the normal clotting reagent for the sample of blood to be analysed. Compartment C contains 4X superparamagnetic particles 4 and a clotting reagent with a known long clotting time in any type of blood. The ratio of particles between the compartments may vary from that shown above and is chosen such that the individual clotting times of each compartment may be determined.

When this chamber 21 is used and each compartment is filled at the same time with a sample of blood and the measurement sequence started. The relative times at which particles 4 should stop moving in compartments A and C are known, and the time which particles 4 stop moving in compartment B is to be determined. Because the number of particles 4 in each compartment is different it is possible to distinguish in which compartment particles 4 have stopped moving by the change in the differential sensor output as particles 4 stop moving in each compartment.

FIG. 9 shows an example output for the apparatus when using the chamber 2 illustrated in FIG. 8. The graph shows an initial sharp increase in output on introduction of a sample of blood. After a period of time the output drops sharply by an amount indicative that a quantity X of superparamagnetic particles 4 has stopped moving, indicating that the blood in compartment A has clotted. After a further period the output falls by an amount indicative that the quantity 2X of superparamagnetic particles 4 has stopped moving, indicating that the blood in compartment B has clotted and, finally, after a third period the output falls by a further amount representative of an amount 4X of superparamagnetic particles 4 has stopped moving in the chamber 2. This third fall indicates that blood in compartment C has clotted.

The time to clot for compartments A and C can be used to calibrate the apparatus and make any necessary modification to the time measured to clot for compartment B.

The above embodiments confer significant advantages over prior art apparatus and methods. By virtue, in particular, of the very sharp cut off in sensor output when a sample of blood clots it is possible to make an accurate measurement of coagulation time using only a very small quantity of blood, typically about 2 µl.

Whilst the apparatus is particularly suited to determining the coagulation time of blood, it can be used to analyse other types of liquid as well.

Equivalents

The present invention provides in part methods and devices comprising magnetic particles for monitoring the coagulation state of a sample. While specific embodiments of the subject invention have been discussed, the above specification is illustrative and not restrictive. Many variations of the invention will become apparent to those skilled in the art upon review of this specification. The appendant claims are not intended to claim all such embodiments and variations, and the full scope of the invention should be determined by reference to the claims, along with their full scope of equivalents, and the specification, along with such variations.

All publications and patents mentioned herein are hereby incorporated by reference in their entireties as if each individual publication or patent was specifically and individually indicated to be incorporated by reference. In case of conflict, the present application, including any definitions herein, will control.

We claim:

1. A device for determining the coagulation state of a sample comprising:
    a sample chamber defining a volume for receiving a sample to be analysed, the sample chamber having a sample chamber major axis;
    at least one particle disposed within the chamber volume wherein the at least one particle comprises at least one material which experiences a force when placed in a magnetic field;
    a first electromagnet and a second electromagnet for applying a magnetic field to at least part of the chamber volume, the first electromagnet being spaced apart from the second electromagnet by the sample chamber, the first electromagnet having a first electromagnet major axis, the second electromagnet having a second electromagnet major axis, and the first electromagnet major axis and the second electromagnet major axis being parallel to the sample chamber major axis;
    at least one sensor operative to detect a response, along the sample chamber major axis, of the at least one particle to the magnetic field; and
    a processor configured to determine the coagulation state of the sample based on the response, along the sample chamber major axis, of the at least one particle to the magnetic field.

2. The device of claim 1, wherein said device further comprises a display.

3. The device of claim 1, wherein said device displays a value that is correlated with a disturbance of hemostasis.

4. The device of claim 1, wherein said device displays a clotting time and/or an INR value.

5. The device of claim 1, wherein said sample may be blood or plasma.

6. The device of claim 1, further comprising a filling chamber.

7. The device of claim 6, further comprising a filling device for filling the chamber.

8. The device of claim 7, where said filling device comprises a capillary.

9. The device of claim 1, wherein said material which experiences a force when placed in a magnetic field may be ferromagnetic, paramagnetic, or superparamagnetic.

10. The device of claim 1, where the at least one particle is generally spherical.

11. The device of claim 1, where the at least one particle has a size in the range of about 2 to about 500 µm.

12. The device of claim 11, wherein the at least one particle has a size in the range of about 2 to about 20 µm in at least one direction.

13. The device of claim 1, wherein the at least one particle comprises two or more different materials and wherein at least one material experiences a force when exposed to a magnetic field.

14. The device of claim 1, wherein more than one particle is disposed in said volume.

15. The device of claim 1, wherein said magnetic field is between about 1 and about 100 mT.

16. The device of claim 15, wherein said magnetic field is between about 10 and about 50 mT.

17. The device of claim 16, wherein the magnetic field is between about 10 to about 20 mT.

18. The device of claim 1, wherein the device further comprises at least one reagent disposed within a chamber prior to introduction of a sample into the device.

19. The device of claim 18, wherein the reagent is selected from the group consisting of: clotting agents, anti-clotting agents, and reagents suitable for measurement of a disturbance of hemostasis.

20. The device of claim 1, wherein each electromagnet produces a constant field and is activated alternately with a direct current.

21. The device of claim 1, wherein the sensor is a Hall Effect sensor.

22. The device of claim 1, wherein the device further comprises circuitry for measuring the time elapsed from introduction of a sample until a change in coagulation state is detected.

23. The device of claim 1, wherein the device further comprises a control means.

24. The device of claim 1, wherein the chamber has a volume of less than about 25 µl.

25. The device of claim 24, wherein the chamber has a volume less than about 5 µl.

26. The device of claim 1, wherein the device further comprises a means for heating the chamber.

27. The device of claim 1, wherein the chamber is formed in a disposable support strip which is removable from the device.

28. The device of claim 1, wherein the ratio of the chamber volume to the particle volume is about 30 or greater.

29. A method of determining the coagulation state of a sample comprising:

provided a sample in a sample chamber, the sample chamber having a major axis, and the sample containing at least one particle comprising a material which experiences a force when placed in a magnetic field;

applying a magnetic field to said sample using a first electromagnet and a second electromagnet, the first electromagnet being spaced apart from the second electromagnet by the sample chamber, the first electromagnet having a first electromagnet major axis, the second electromagnet having a second electromagnet major axis, and the first electromagnet major axis and the second electromagnet major axis being parallel to the sample chamber major axis; and using a sensor to detect a response, along the sample chamber major axis, of the at least one particle to the magnetic field to determine the coagulation state of the sample.

* * * * *